(12) United States Patent
Esser et al.

(10) Patent No.: US 6,268,389 B1
(45) Date of Patent: *Jul. 31, 2001

(54) TREATMENT OF URINARY INCONTINENCE BY ADMINISTRATION OF $\alpha_{1L}$-ADRENOCEPTOR AGONISTS

(75) Inventors: Franz Esser; Helmut Staehle, both of Ingelheim am Rhein; Sven Luettke, Ockenheim, all of (DE); Ikunobu Muramatsu, Yoshida-gun (JP); Hisato Kitagawa, Osaka Prefecture (JP); Shuji Uchida, Toyonaka (JP)

(73) Assignee: Boehringer Ingelheim KG, Ingelheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/227,944

(22) Filed: Jan. 11, 1999

Related U.S. Application Data

(63) Continuation of application No. 08/913,900, filed as application No. PCT/EP96/01568 on Apr. 13, 1996.

(30) Foreign Application Priority Data

Apr. 20, 1995 (DE) .............................. 197 14 579

(51) Int. Cl.$^7$ .......................... A61N 13/00; A61N 13/10; A61K 31/4168
(52) U.S. Cl. .................... 514/398; 548/331.5; 548/333.1
(58) Field of Search ............................ 548/331.5, 315.1; 514/398

(56) References Cited

U.S. PATENT DOCUMENTS

| | | | |
|---|---|---|---|
| 3,081,222 | * 3/1963 | Hageman et al. | 548/331.5 X |
| 3,202,660 | 8/1965 | Zeile et al. | 548/323.5 X |
| 3,758,476 | * 9/1973 | Rippel et al. | 548/315.1 X |
| 3,931,216 | 1/1976 | Franzmair . | |
| 3,995,050 | * 11/1976 | Amselem | 548/333.1 X |
| 4,142,051 | 2/1979 | Franzmair | 548/315 |
| 4,213,995 | 7/1980 | Staehle et al. . | |
| 4,226,713 | 10/1980 | Goldberg | 23/230 B |
| 4,226,773 | 10/1980 | Kynel | 424/273 P |
| 4,287,201 | 9/1981 | Olson et al. | 424/273 R |
| 4,293,564 | * 10/1981 | Stahle et al. | 548/333.1 X |
| 4,355,033 | * 10/1982 | Ramuz | 424/256 |
| 4,450,170 | * 5/1984 | Beeley et al. | 548/333.1 X |
| 4,461,904 | * 7/1984 | York | 548/333.1 |
| 4,492,709 | 1/1985 | Purcell | 548/315 X |
| 4,558,063 | * 12/1985 | Beeley et al. | 514/402 |
| 4,587,257 | 5/1986 | DeSantis et al. | 514/392 |
| 4,861,789 | * 8/1989 | Berge et al. | 514/370 |
| 5,130,441 | * 7/1992 | Gluchowski | 548/331.5 |
| 5,237,072 | * 8/1993 | Gluchowski | 548/323.5 |
| 5,866,579 | * 2/1999 | Wong et al. | 514/259 |

FOREIGN PATENT DOCUMENTS

| | | |
|---|---|---|
| 0071554 | * 3/1970 | (DE) . |
| 1 929 950 | 3/1970 | (DE) . |
| 2 316 377 | 10/1974 | (DE) . |
| 28 06 811 A1 | 8/1979 | (DE) . |
| 28 54 659 A1 | 7/1980 | (DE) . |
| 0 030 616 B1 | 6/1981 | (EP) . |
| 0 070 084 A2 | 1/1983 | (EP) . |
| 0 081 923 A2 | 6/1983 | (EP) . |
| 0 081 924 A1 | 6/1983 | (EP) . |
| 0 073 394 A1 | 9/1983 | (EP) . |
| 0 117 102 A1 | 8/1984 | (EP) . |
| 0 149 140 A2 | 7/1985 | (EP) . |
| 0 236 636 A3 | 9/1987 | (EP) . |
| 0 416 841 A3 | 3/1991 | (EP) . |
| 0 599 697 A1 | 6/1994 | (EP) . |
| 0 682 028 A1 | 11/1995 | (EP) . |
| WO 88/07995 A2 | 10/1988 | (WO) . |
| 94/08040 A1 | 4/1994 | (WO) . |

OTHER PUBLICATIONS

Nordling, J. et al; "Sympathetic Influence on Striated Urethral Sphincter in Urinary Incontinence"; Prog. Clin. Biol. Res., vol. 78, pp. 101–103; 1981.

Randall, W. C., et al; "Multiple Central Alpha2 Adrenoceptors Of Avian And Mammalian Species"; Biochem. Pharmacol., vol. 32, No. 12, pp. 1933–1940; 1983.

Kontani, H. et al; "Effects of Adrenergic Agonists on an Experimental Urinary Incontinence Model in Anesthetized Rabbits"; Jpn. J. Pharmacol, vol. 58, No. 4, pp. 339–346; 1992.

Van Savage, J. G., et al; "Effects of Alpha–Adrenergic Agonist on Neobladder Water and Electrolyte Transport"; Urology, vol. 43, No. 3, pp. 324–327, 1994.

J. P. Hieble, et al; "Recent Progress in the Pharmacotherapy of Diseases of the Lower Urinary Tract"; Eur. J. Med. Chem.; pp. 269s–98s; 1995.

Lehman, D., et al; "Verfahren zur Herstellung von Imidazolin–2–Derivaten"; Patentschrift 71 554.

* cited by examiner

Primary Examiner—Floyd D. Higel
(74) Attorney, Agent, or Firm—R. P. Raymond; T. X. Witkowski; A. R. Stempel

(57) ABSTRACT

The present invention relates to the use of $\alpha_{1L}$-agonists for treating urinary incontinence.

14 Claims, No Drawings

TREATMENT OF URINARY INCONTINENCE BY ADMINISTRATION OF $\alpha_{1L}$-ADRENOCEPTOR AGONISTS

RELATED APPLICATIONS

This is a continuation under 37 CFR 1.53(b) of prior application Ser. No. 08/913,900, filed on Feb. 26, 1998, pursuant to 35 USC 371 and claiming benefit, under 35 USC 120, from PCT/EP96/01568, filed Apr. 13, 1996.

The present invention relates to the use of $\alpha_{1L}$-agonists for treating urinary incontinence, particularly stress incontinence.

The cause of stress incontinence in women is usually weakness of the pelvic floor, e.g. after numerous difficult births. However, it may also be due to nerve disorders of the pelvic floor, a congenitally short urethra or, occasionally, damage to the sphincter caused by surgery. The reduction in the oestrogen levels post-menopause further encourages stress incontinence.

The term stress incontinence refers to a sudden loss of urine, which is caused by incompetence of the bladder outlet during unobtrusive movement of the bladder as a result of interabdominal increases in pressure due to coughing, pressing, sneezing, heavy lifting, etc.

Surprisingly, it has been found that the (XL-subtype of the adrenergic receptor has a significant effect on the continence mechanism of urether tonicisation.

The invention relates to the use of $\alpha_{1L}$-adrenoceptor agonists for treating urinary incontinence, particularly stress incontinence, and for preparing drugs for treating urinary incontinence, particularly stress incontinence. It is particularly interesting to use amino imidazolines of general formula

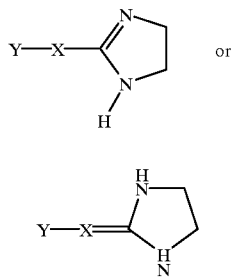

and the pharmacologically acceptable acid addition salts thereof.

In general formula I
Y denotes an optionally substituted phenyl or napthyl group or
Y denotes a 5- or 6-membered, optionally fully unsaturated, optionally substituted heterocyclic ring which contains oxygen, sulphur or nitrogen as heteroatoms, and
X denotes —NH—, —CH$_2$—, —OCH$_2$—, —O—CHCH$_3$—, —CH=N—NH—, —N=N— or —NZ—, wherein Z=—CH$_2$—CH=CH$_2$ or cyclopropylmethyl.

Preferred compounds are those wherein X is —NH— and/or Y is an optionally substituted thienyl, furyl, pyrrole, tetrahydropyrrole, pyridyl, pyrazinyl, pyranyl, 1,3-thiazolyl, imidazolyl, imidazolinyl, 1,2,4-triazolyl, 1,2,3-triazolyl, tetrazolyl, isothiazolyl, pyrimidinyl, thiazolyl, thiadiazinyl or piperidinyl, bound to the group X via a C atom. It is preferred to use tiamenidine.

Preferred compounds for this purpose are imidazolines of general formula

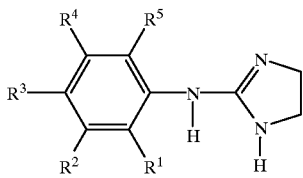

or imidazolines of general formula

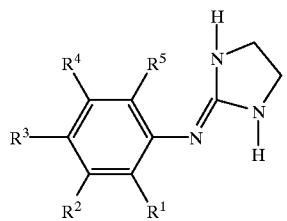

wherein
R$^1$, R$^2$, R$^3$, R$^4$ and R$^5$ denote, independently of one another: hydrogen, C$_{1-6}$-alkyl, preferably C$_{1-4}$-alkyl, most preferably methyl, C$_{3-6}$-cycloalkyl, preferably cyclopropyl, C$_{1-6}$-alkoxy, preferably C$_{1-4}$-alkoxy, most preferably methoxy, halogen, preferably chlorine or bromine, —CF$_3$, —OCF$_3$ or —NR R$^7$ wherein
   R$^6$ denotes hydrogen, C$_{3-6}$-cycloalkyl, C$_{1-6}$-alkyl, preferably C$_{1-4}$-alkyl, most preferably methyl, or C$_{2-4}$-acyl, most preferably acetyl,
   R$^7$ denotes hydrogen, C$_{3-6}$-cycloalkyl, preferably cyclopropyl, C$_{1-6}$-alkyl, preferably C$_{1-4}$-alkyl, most preferably methyl, or C$_{2-4}$-acyl, most preferably acetyl; or
   R$^6$ and R$^7$ together with the nitrogen atom form a 5- or 6-membered saturated or unsaturated ring which may contain up to two further heteroatoms selected from oxygen, sulphur or nitrogen, whilst each additional nitrogen atom may be substituted by C$_{1-4}$-alkyl, preferably methyl;
   or R$^6$ and R$^7$ together with the nitrogen atom form phthalimido;
or R$^1$ and R$^2$ together form a fused pyrazole of formula

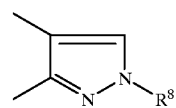

wherein R$^8$ is C$_{1-3}$-alkyl, preferably methyl;
or a fused thiadiazole of formula

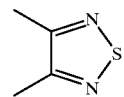

wherein R$^3$, R$^4$ and R$^5$ are as hereinbefore defined, and preferably denote hydrogen, and the pharmacologically acceptable acid addition salts thereof.

Formulae I and I' and Ib and II are equivalent tautomeric structures. The preparation of one structure (e.g. Ib) includes the other structure (e.g. II) in each case.

Also preferred are imidazolines of general formula Ib

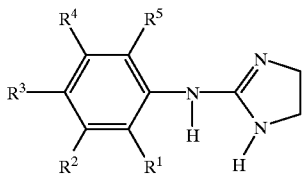

wherein
$R^1$ denotes hydrogen, ethyl, methyl, fluorine, chlorine, bromine or $CF_3$,
$R^2$ denotes methyl, fluorine, chlorine, bromine or —$NR^6R^7$, wherein
$R^6$ denotes hydrogen, $C_{1-4}$-alkyl, preferably methyl, $C_{2-4}$-acyl, preferably acetyl and
$R^7$ denotes hydrogen, $C_{1-4}$-alkyl, preferably methyl, $C_{2-4}$-acyl, preferably acetyl or
$R^6$ and $R^7$ together with the nitrogen atom form phthalimido;
$R^3$ denotes hydrogen, fluorine, chlorine, bromine, $C_{1-4}$-alkyl, preferably methyl, $NH_2$ or cyclopropyl;
$R^4$ denotes hydrogen, $C_{1-4}$-alkyl, preferably methyl, fluorine, chlorine, bromine or $CF_3$;
$R^5$ denotes hydrogen, $C_{1-4}$-alkyl, preferably ethyl or methyl, fluorine, chlorine, bromine or $CF_3$; or
$R^1$ and $R^2$ together form a fused pyrazole of formula

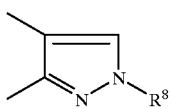

wherein $R^8$ is methyl,
or a fused thiadiazole of the formula

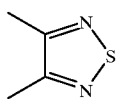

wherein $R^3$, $R^4$ and $R^5$ are as hereinbefore defined, and preferably represent hydrogen; particularly those wherein
$R^1$ is hydrogen or methyl;
$R^2$ is methyl, chlorine, $CF_3$, $NH_2$ or $N(CH_3)_2$;
$R^3$ is hydrogen, methyl, chlorine or bromine;
$R^4$ is hydrogen;
$R^5$ is hydrogen, methyl, methoxy, chlorine or bromine.

Particular mention should be made of the use of
2-(3-dimethylamino-2-methylphenylimino) imidazolidine,
2-(6-bromo-3-dimethylamino-2-methylphenylimino) imidazolidine,
2-(5-amino-2-chloro-4-methylphenylimino)-imidazolidine,
2-(3-amino-2-methylphenylimino)-imidazolidine or
2-(2-chloro-5-trifluoromethylphenylimino)-imidazolidine.

Examples of heterocyclic groups —$NR^6R^7$ are as follows: pyrrole, $\Delta^2$-pyrroline, $\Delta^3$-pyrroline, tetrahydropyrrole, pyrrolidine, pyrrolidinone, imidazole, imidazoline, 1,3-thiazole, piperidine, piperazine, 4-$C_{1-4}$-aclkylpiperazine, $C_{1-4}$-alkylpiperazine, 2,5-diketopiperazine, preferably N-methylpiperazine, morpholine, thiomorpholine, phthalimido or succinimido.

Examples of alkyl within the above definitions, including those which are components of other groups, are branched or unbranched $C_{1-6}$-alkyl groups, e.g. methyl, ethyl, n-propyl, isopropyl, isobutyl, n-butyl, isobutyl, sec.-butyl and tert.-butyl, n-pentyl, isopentyl, neopentyl, hexyl and isohexyl.

Cycloalkyl generally represents a saturated cyclic hydrocarbon group having 3 to 6 carbon atoms which may optionally be substituted with a halogen atom or several halogen atoms, a hydroxy group, an alkyl group, preferably methyl, which may be the same as or different from one another. Examples include cyclopropyl, cyclobutyl, cyclopentyl, cyclopentenyl, cyclohexyl, cyclohexenyl.

Some of the imidazolines defined in general formula Ib are new. The invention therefore also relates to new substituted 2-phenylimino-imidazolidines, their use in pharmaceutical compositions and to processes for preparing them.

2-(Phenylimino)-imidazolidines, the preparation thereof and their use as pharmaceutical compositions are known, for example from German Patent Application Nos. DE-OS-19 29 950 and DE-OS-23 16 377, in which the hypotensive properties of the compounds described are particularly emphasised.

New substituted 2-(phenylimino)-imidazolidines of general formula II

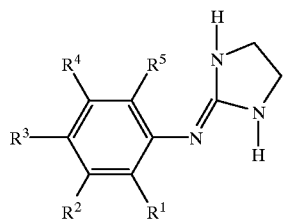

have surprising pharmacological properties and are particularly suitable for treating urinary incontinence.

The invention thus relates to compounds of general formula II

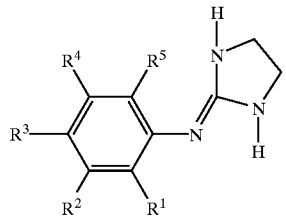

wherein
$R^1$ denotes hydrogen, $C_{1-6}$-alkyl, preferably $C_{1-4}$-alkyl, most preferably methyl, $C_{3-6}$-cycloalkyl, preferably cyclopropyl, $C_{1-6}$-alkoxy, preferably $C_{1-4}$-alkoxy, most preferably methoxy, halogen, preferably chlorine or bromine, —$CF_3$ or —$OCF_3$;
R denotes -$NR^6R^7$ wherein
$R^6$ denotes hydrogen, $C_{3-6}$-cycloalkyl, $C_{1-6}$-alkyl, preferably $C_{1-4}$-alkyl, most preferably methyl, $C_{2-4}$-acyl, most preferably acetyl;
$R^7$ denotes hydrogen, cyclopropyl, $C_{3-6}$-cycloalkyl, $C_{1-6}$-alkyl, preferably $C_{1-4}$-alkyl, most preferably methyl, $C_{2-4}$-acyl, most preferably acetyl; or $R^6$ and $R^7$ together with the nitrogen atom form a 5- or 6-membered saturated or unsaturated ring which may contain up to two additional heteroatoms selected from the group of oxygen, sulphur or nitrogen, whilst each additional nitrogen atom may be substituted by $C_{1-4}$-alkyl, preferably methyl; or $R^6$, and $R^7$ together with the nitrogen atom from phthalimido;

$R^3$ denotes hydrogen, halogen, $C_{1-6}$-alkyl, preferably $C_{1-4}$-alkyl, most preferably methyl, $C_{1-6}$-alkoxy, preferably $C_{1-4}$-alkoxy, most preferably hydrogen, methoxy, —$CF_3$ or —$OCF_3$;

$R^4$ denotes hydrogen, $C_{1-4}$-alkyl, preferably $C_{1-4}$-alkyl, most preferably methyl, hydrogen or halogen;

$R^5$ denotes hydrogen, $C_{1-6}$-alkyl, preferably $C_{1-4}$-alkyl, most preferably methyl, $C_{1-6}$-alkoxy, preferably $C_{1-4}$-alkoxy, most preferably methoxy, halogen, —$CF_3$ or —$OCF_3$, and the pharmacologically acceptable acid addition salts thereof, with the exception of 2-(3-diethylamino-2-methyl)-imidazolidine.

Preferred compounds of general formula II are those wherein
$R^1$ denotes hydrogen, $C_{1-4}$-alkyl, cyclopropyl, $C_{1-4}$-alkoxy, halogen, $CF_3$ or —$OCF_3$;
$R^2$ denotes —$NR_6R_7$ wherein
$R^6$ is hydrogen, $C_{3-6}$-cycloalkyl, $C_{1-4}$-alkyl or acetyl,
$R^7$ is hydrogen, cyclopropyl $C_{1-4}$-alkyl or acetyl, or
$R^6$ and $R^7$ together with the nitrogen atom form phthalimido;
$R^3$ is hydrogen, halogen, $C_{1-4}$-alkyl, $C_{1-4}$-alkoxy, $CF_3$ or —$OCF_3$;
$R^4$ is hydrogen, $C_{1-4}$-alkyl, methyl, halogen;
$R^5$ is hydrogen, $C_{1-4}$-alkyl, $C_{1-4}$-alkoxy, halogen, $CF_3$ or —$OCF_3$; particularly those wherein
$R^1$ is hydrogen, $C_{1-3}$-alkyl, n-butyl, isobutyl, sec.-butyl, preferably methyl, cyclopropyl, $C_{1-3}$-alkoxy, preferably methoxy, halogen, preferably chlorine or bromine, $CF_3$;
$R^2$ denotes —$NR_6R_7$ wherein
$R^6$ is hydrogen, cyclopropyl, $C_{1-4}$-alkyl, preferably methyl,
$R^7$ denotes hydrogen, $C_{1-4}$-alkyl, preferably methyl, or $R^6$ and
$R^7$ together with the, nitrogen atom form phthalimido;
$R^3$ denotes hydrogen, $C_{1-3}$-alkyl, n-butyl, isobutyl, sec.-butyl, preferably methyl, cyclopropyl, $C_{1-3}$-alkoxy, preferably methoxy, halogen, preferably chlorine or bromine, $CF_3$;
$R^4$ denotes hydrogen, $C_{1-3}$-alkyl, n-butyl, isobutyl, sec.-butyl, preferably methyl, cyclopropyl, $C_{1-3}$-alkoxy, preferably methoxy, halogen, preferably chlorine or bromine;
$R^5$ denotes hydrogen, $C_{1-3}$-alkyl, n-butyl, isobutyl, sec.-butyl, preferably methyl, cyclopropyl, $C_{1-3}$-alkoxy, preferably methoxy, halogen, preferably chlorine or bromine, $CF_3$; particularly those wherein
$R^1$ is hydrogen or methyl,
$R^2$ is —$NR^6R^7$ wherein
$R^6$ and $R^7$ independently of each other denote hydrogen, methyl or methoxy or
$R^6$ and $R^7$ together with the nitrogen atom form phthalimido;
$R^3$ denotes hydrogen, methyl, fluorine, chlorine or bromine;
$R^4$ denotes hydrogen,
$R^5$ denotes hydrogen, methyl, chlorine or bromine;
and the pharmacologically acceptable acid salts thereof, especially the hydrobromides or hydrochlorides thereof.

Particular mention should be made of the following compounds, for example:
2-(3-dimethylamino-2-methylphenylimino) imidazolidine,
2-(6-bromo-3-dimethylamino-2-methylphenylimino) imidazolidine,
2-(5-amino-2-chloro-4-methylphenylimino)-imidazolidine and
2-(3-amino-2-methylphenylimino)-imidazolidine.

The compounds of general formula I and II may be prepared according to analogous processes known per se from the prior art. A selection of the preferred processes are shown in the following synthetic schemes with reference to concrete Examples.

Synthetic Scheme I

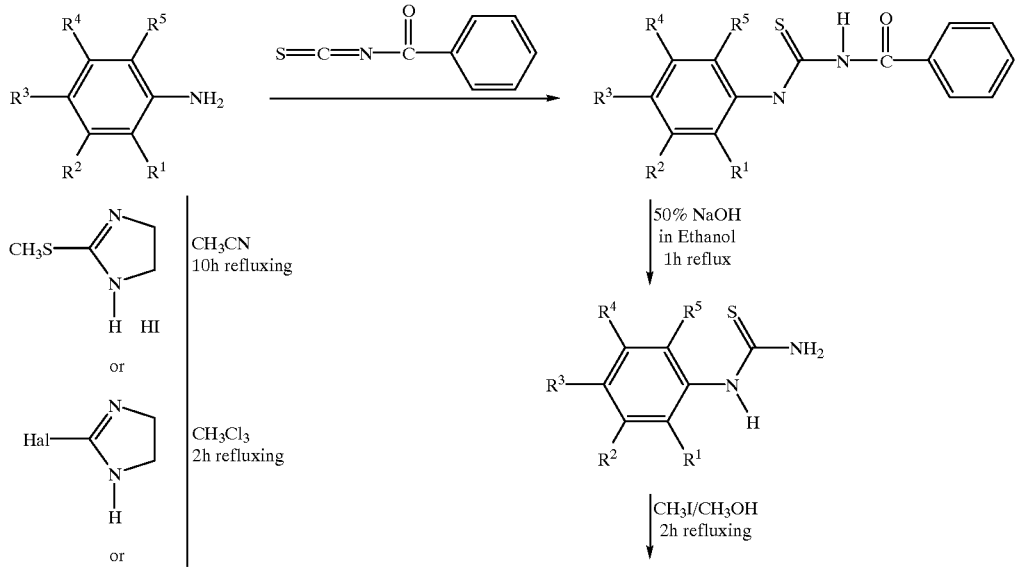

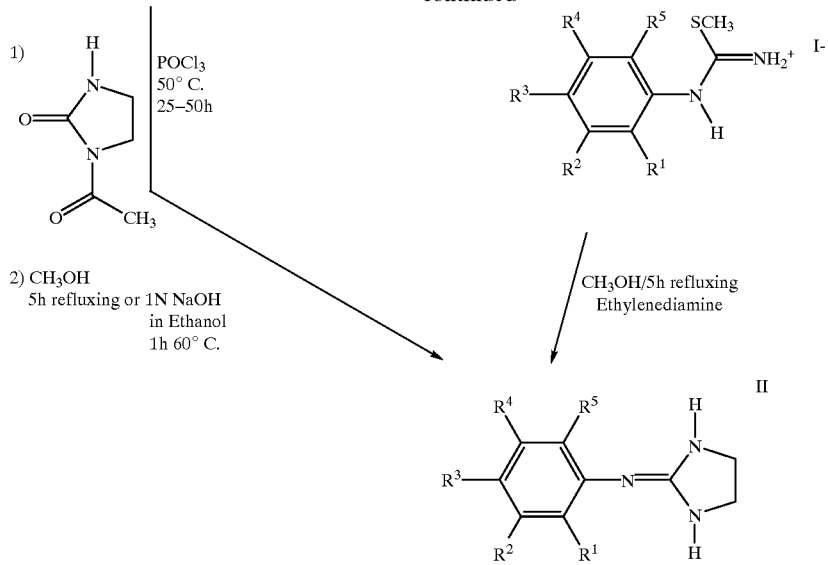

The preferred processes for preparing the compounds according to the invention will be explained with reference to individual Examples.

The methylation of the starting material, 2-methyl-3-nitro-aniline, may also be carried out analogously to the Leuckart-Wallach reaction using HCOOH/CH$_2$O or using dimethylcarbonate instead of dimethylsulphate.

Compound 2 can be prepared by bromination of compound 1 under conventional reaction conditions

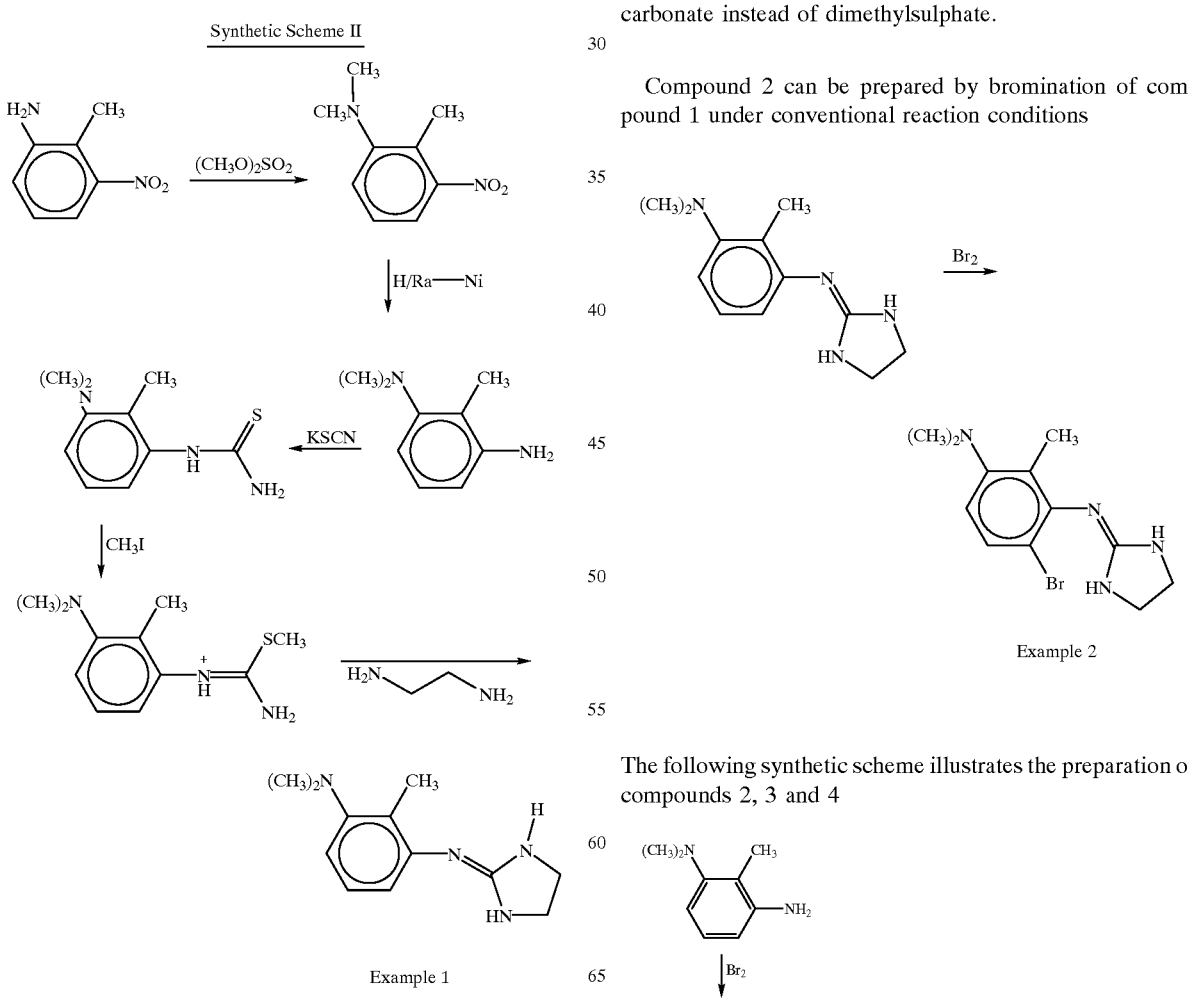

The following synthetic scheme illustrates the preparation of compounds 2, 3 and 4

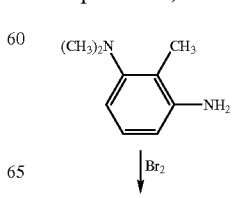

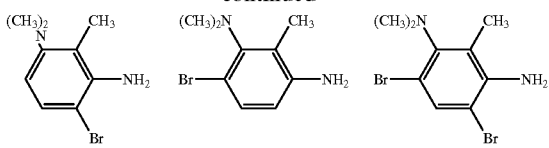

Example 2     Example 3     Example 4

Other alternative methods of synthesis are illustrated below.

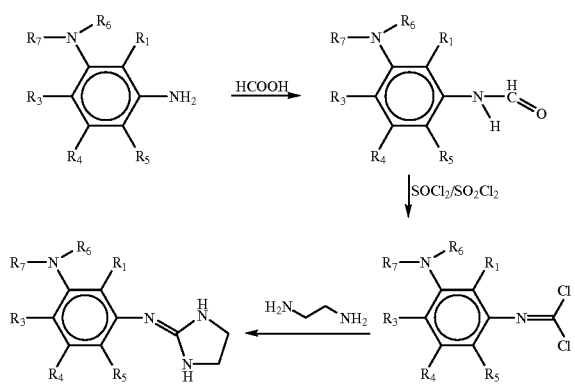

Compound 5 and compounds of similar structure can be prepared analogously to a method described by N. R. Ayyangar (Synthesis 1987, 64).

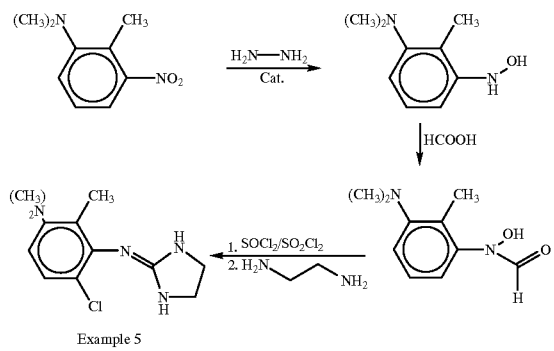

Example 5

EXAMPLE 1

2-(3-Dimethylamino-2-methylphenylimino) imidazolidine

1st Step:

83.6 g of 2-methyl-3-nitroaniline, 190 g of $K_2CO_3$ and 260 ml of water are together heated to 100° C. 27 ml of dimetbylsulphate are added dropwise over 1 hour, then the mixture is heated for a further hour. After cooling to ambient temperature, the top layer is removed and the aqueous phase remaining is extracted four times with ether.

The combined ether extracts are combined with the upper layer, dried with $MgSO_4$ and evaporated down in vacuo. 73 g of N,N-dimethyl-2-methyl-3-nitroaniline are obtained.

2nd Step:

73 g of N,N-dimethyl-2-methyl-3-nitroaniline are dissolved in 800 ml of methanol and hydrogenated at 20° C under 5 bar of hydrogen using Raney nickel as catalyst. 57 g of 3-dimethylamino-2-methylaniline are obtained.

3rd Step:

57 g of 3-dimethylamino-2-methyl-aniline, 1.15 litres of acetone, 36.6 g of KSCN and 43.8 ml of benzoylchloride are refluxed together for 3 hours. After cooling to ambient temperature the reaction mixture is poured onto 2.4 kg of crushed ice. The precipitate obtained is heated to 60° C. for 2 hours together with 85 g of KOH, 85 ml of water and 255 ml of ethanol. After the addition of 850 ml of water the ethanol is distilled off under reduced pressure. After the resulting precipitate has been worked up, 72 g of N-(3-dimethylamino-2-methylphenyl)-thiourea are obtained.

4th Step:

72 g of the thiourea from Step 3 are taken up in 345 ml of methanol and after the addition of 22.6 ml of methyliodide the mixture is refluxed for 2 hours. The resulting solution is evaporated down under reduced pressure; 120 g of N-(3-dimethylamino-2-methylphenyl)-S-methyl-isothiourea hydroiodide are obtained.

5th Step:

120 g of the thiourea from Step 4 in 350 ml of methanol are combined with 14.4 ml of 1,2-diaminoethane and refluxed for 17 hours. The reaction mixture is then evaporated down in vacuo and the residue is taken up in water. The pH is adjusted to 7 using dilute hydrochloric acid. The aqueous phase is extracted 3 times with ethyl acetate. Then the aqueous phase is made alkaline with 5N NaOH and extracted a further 3 times with ethyl acetate, these extracts are combined, dried with $MgSO_4$ and evaporated down in vacuo. An oil is obtained which is chromatographed over silica gel (eluant toluene, dioxane, ethanol, ammonia 10:8:3:1="Super-T").

17.9 g of 2-(3-dimethylamino-2-methylphenyl-imino)-imidazolidine are obtained. Melting point 116–118° C.

EXAMPLE 2

2-(6-Bromo-3-dimethylamino-2-methylphenylimino) imidazolidine 6.55 g of 2-(3-Dimethylamino-2-methylphenyl-imino)-imidazolidine are dissolved in 75 ml of chloroform and 1.53 ml of bromine are added, with stirring, at 0° C. After 2 hours at 0° C. the solution is evaporated down under reduced pressure and the residue thus obtained is mixed with dilute hydrochloric acid. The aqueous solution is extracted twice with ether, then the aqueous phase is made alkaline with dilute NaOH and extracted three more times with ether. The combined ether extracts are evaporated down under reduced pressure and the residue remaining is worked up by chromatography (silica gel, eluant "Super-T" (Example 13).

3.4 g of 2-(6-bromo-3-dimethylamino-2-methyl-phenylimino)-imidazolidine are obtained, Mp. 157–158° C., as a white powder.

The following compounds were prepared analogously to the processes described:

2-(4-bromo-3-dimethylamino-2-methylphenylimino)-imidazolidine 2-(4, 6-dibromo-3-dimethylamino-2-methylphenylimino)-imidazolidine 2-(6-chloro-3-dimethylamino-2-methylphenylimino)-imidazolidine 2-(3-acetylamino-6-chlorophenylimino)-imidazolidine, Mp. 236–238° C.

2-(2-methyl-3-phthalimidophenylimino)-imidazolidine, Mp. 189–190° C.

2-(6-chloro-3-phthalimidophenylimino)-imidazolidine, Mp. 239–241° C.
2-(5-amino-2-chloro-4-methylphenylimino)-imidazolidine, Mp. 155–157° C. 2-(3-amino-4-fluorophenylimino)-imidazolidine, (2HCl), Mp. 222° C.
2-(3-amino-4-methylphenylimino)-imidazolidine, (HCl), 2-(3-amino-6-methylphenylimino)-imidazolidine, (HCl), Mp. 194–196° C.
2-(3-amino-6-chlorophenylimino)-imidazolidine, (HCl), Mp. 197–198° C.
2-(3-amino-4,6-dibromo-2-methylphenylimino)-imidazolidine, Mp. 154–155° C.
2-(3-amino-2-methylphenylimino)-imidazolidine, (HCl), Mp. 204–206° C.

The following compounds are specifically mentioned by name:
2-(2, 6-diethylphenyl-imino)-imidazolidine
2-(2-chloro-6-methylphenylimino)-imidazolidine
2-(2,6-dichloro-phenylimino)-imidazolidine
2-(2-chloro-4-methylphenylimino)-imidazolidine
2-(2,4-dichlorophenylimino)-imidazolidine
2-(2-chloro-5-trifluoromethylphenylimino)-imidazolidine
2-(5-fluoro-2-methylphenylimino)-imidazolidine
2-(3-bromo-2-methylphenylimino)-imidazolidine
2-(2-chloro-3-methylphenylimino)-imidazolidine
2-(2-fluoro-6-trifluoromethylphenylimino)-imidazolidine
2-(2-chloro-4-cyclopropylphenylimino)-imidazolidine
2-(4-amino-3,5-dibromophenylimino)-imidazolidine
2-(3-fluoro-4-methylphenylimino)-imidazolidine
2-(6-bromo-2-fluorophenylimino)- imidazolidine
4-(2-imidazolin-2-ylamino)-2-methylindazole
5-chloro-4-(imidazolin-2-yl-amino)-benzothiadiazole (Tizanidine)
2-[(2-chloro-4-methyl-3-thienyl) amino]-2-imidazoline (Tiamenidine)
2-(2,5-dichlorophenylimino)-imidazolidine The compounds of general formulae I and II according to the invention may be converted into their physiologically acceptable acid addition salts in the usual way. Examples of acids suitable for salt formation include, for example, inorganic acids such as hydrochloric acid, hydrobromic acid, hydiodic acid, hydrofluoric acid, sulphuric acid, phosphoric acid, nitric acid or organic acids such as acetic acid, propionic acid, butyric acid, caproic acid, capric acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicylic acid, ascorbic acid, methanesulphonic acid and ethanephosphonic acid.

The corresponding hydrobromides and hydrochlorides are preferred as the acid addition salts.

Pharmaceutical compositions comprising the compounds described may be used in the form of capsules, suppositories, solutions, syrups, emulsions or dispersible powders. Corresponding tablets may be obtained, for example, by mixing the active substance or substances with known excipients such as inert diluents, e.g. calcium carbonate, calcium phosphate or lactose, disintegrants such as corn starch or alginic acid, binders such as starch or gelatine, lubricants such as magnesium stearate or talc, and/or agents for obtaining delayed release, such as carboxypolymethylene, carboxymethylcellulose, cellulose acetate phthalate, or polyvinyl acetate. The tablets may also consist of several layers.

Coated tablets may be produced accordingly, by coating cores made analogously to the tablets with agents conventionally used for tablet coating, e.g. collidone or shellac, gum arabic, talc, titanium dioxide or sugar. In order to achieve delayed release or prevent incompatibilities, the core may also consist of several layers. Similarly, the tablet coating may consist of several layers in order to achieve delayed release, and the excipients mentioned for the tablets may be used.

Syrups of the active substances or combinations of active substances according to the invention may additionally contain a sweetener such as saccharin, cyclamate, glycerol or sugar and a flavour enhancer, e.g. a flavouring such as vanillin or orange extract. They may also contain suspension adjuvants or thickeners such as sodium carboxymethylcellulose, wetting agents, e.g. condensation products of fatty alcohols with ethylene oxide, or preservatives such as p-hydroxybenzoates.

Injectable solutions are prepared in the usual way, e.g. by adding preservatives such as p-hydroxybenzoates or stabilisers such as alkali metal salts of ethylenediamine tetraacetic acid and are then transferred into injection vials or ampoules.

The capsules containing the active substance or combination of active substances may be prepared, for example, by mixing the active ingredients with inert carriers such as lactose or sorbitol and packaging the mixture in gelatine capsules.

Suitable suppositories may be produced, for example, by mixing with carriers provided for this purpose such as neutral fats of polyethyleneglycol or derivatives thereof.

For transdermal application the active substances according to the invention may be incorporated in suitable carriers (plasters), e.g. made of polyacrylates. Suitable adjuvants may be used in order to increase the release rate.

For oral administration a dosage of 1 to 50 mg is proposed as a therapeutically single dose.

Example A: Tablets

| | |
|---|---|
| 2-(3-Dimethylamino-2-methylphenylimino)-imidazolidine.HBr | 10 mg |
| Lactose | 65 mg |
| Corn starch | 125 mg |
| sec.Calcium phosphate | 40 mg |
| Soluble starch | 3 mg |
| Magnesium stearate | 4 mg |
| Colloidal silica | 4 mg |
| Total | 251 mg |

Preparation:

The active substance is mixed with some of the excipients, kneaded intensively with an aqueous solution of the soluble starch and granulated with a sieve in the usual way. The granules are combined with the remaining excipients and compressed into tablet cores weighing 250 mg which are then coated in the usual way using sugar, talc and gum arabic.

Example B: Ampoules

| | |
|---|---|
| 2-(3-Dimethylamino-2-methylphenylimino)-imidazolidine.HBr | 1.0 mg |
| Sodium chloride | 18.0 mg |
| Sufficient distilled water to make up to | 2.0 ml |

Preparation:

The active substance and sodium chloride are dissolved in water and transferred into glass ampoules under nitrogen.

Example C: Drops

| 2-(3-Dimethylamino-2-methylphenylimino)-imidazolidine.HBr | 0.02 g |
|---|---|
| Methyl p-hydroxybenzoate | 0.07 g |
| Propyl p-hydroxybenzoate | 0.03 g |
| Sufficient demineralized water to make up to | 100 ml |

Example D: Injectable solution

| 2-(3-Dimethylamino-2-methylphenylimino)-imidazolidine.HBr | 1.5 parts |
|---|---|
| Sodium salt of ethylenediamine tetraacetic acid | 0.2 parts |
| Sufficient distilled water to make up to | 100.0 parts |

Preparation:

The active substance and the sodium salt of ethylenediamine tetraacetic acid are dissolved in sufficient water and topped up to the desired volume with water. The solution is filtered to remove any suspended particles and transferred into 2 ml ampoules under aseptic conditions. Finally, the ampoules are sterilised and sealed. Each ampoule contains 20 mg of active substance.

One advantage of the compounds described is that they act primarily on the urethra and have little or no effect on the cardiovascular system.

The selective pharmacological activity of the compounds according to the invention is demonstrated by the compound of Example 2-2-(6-bromo-3-dimethylamino-2-methylphenylimino)-imidazolidine—and a comparison compound, phenylephrine, by measuring the intraluminal pressure of the urethra and blood pressure in the rabbit.

Female Japanese white rabbits (weighing 3.0 to 3.5 kg) are anaesthetised with urethane (1 g/kg i.p.). A polyethylene cannula is inserted in the urinary bladder by means of a small incision. The changes in the intraluminal pressure are recorded by means of balloon in the urethra which contains about 1.5 ml of water at 37° C. The intraurethral pressure is recorded on a polygraph by means of a pressure-voltage transducer.

The neck is opened up and the carotid artery is cannulated in order to measure the blood pressure and at the same time the trachea is intubated in order to maintain breathing. The changes in blood pressure are recorded on a polygraph by means of a pressure-voltage transducer. Heart rate is measured using a tachometer.

Phenylephrine and the compound of Example 2 are introduced into the Vena femoralis i.v. through a polyethylene cannula. Dosages of 30 μg/kg of phenylephrine are compared with 10 μg/kg of the compound of Example 2.

Compared with phenylephrine the compound of Example 2 according to the invention exhibits a potency which is higher by a factor of 2.73 with regard to the contraction of the urethra and with a duration of effect which is longer by a factor of 4.3. By comparison, the increase in blood pressure with the compound according to the invention is only 1.39 times that of the comparison compound phenylephrine. It is notable that the increase in blood pressure is prolonged only to an insignificant degree (by a factor of 1.17) compared with phenylephrine. These experiments show that the compounds according to the invention have a -selective effect on the urethra. Being selective $\alpha_{1L}$-adrenoreceptor agonists, the compounds according to the invention are suitable for treating problems of urinary incontinence, particularly for treating stress incontinence.

The test results are shown in Table 1.

TABLE 1

| | Contraction of the urethra | Duration of effect | Increase in blood pressure | Duration of effect |
|---|---|---|---|---|
| Phenylephrine | 100 | 100 | 100 | 100 |
| Example 2 | 273 | 430 | 139 | 117 |

Data given in %

Example 2=2-(6-bromo-3-dimethylamino-2-methylphenylimino)imidazoline

What is claimed is:

1. A method for the treatment of urinary incontinence which method comprises administering to a host suffering from urinary incontinence a therapeutically effective amount of an $\alpha_{1L}$-adrenoceptor agonist which is a compound of the formulae Ib

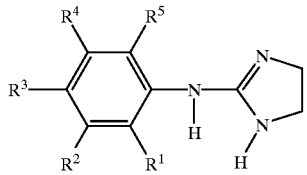

(Ib)

wherein $R^1$, $R^2$, $R^3$, $R^4$ and $R^5$ are each, independently of one another:

hydrogen, $C_{1-6}$-alkyl, $C_{3-6}$-cycloaklyl, $C_{1-6}$-alkoxy, halogen, $—CF_3$, $—OCF_3$, or $—NR^6R^7$, wherein;

$R^6$ is hydrogen, $C_{1-6}$-alkyl, $C_{3-6}$-cycloalkyl or $C_{2-4}$-acyl;

$R^7$ is hydrogen, $C_{1-6}$-alkyl, $C_{3-6}$-cycloalkyl or $C_{2-4}$-acyl; or, $R^6$ and $R^7$ together with the nitrogen between them form a 5- or 6-membered, saturated or unsaturated ring which may contain up to two additional heteroatoms selected from oxygen, sulfur and nitrogen, wherein each additional heteroatom is unsubstituted or substituted by $C_{1-4}$-alkyl; or $R^6$ and $R^7$ together with the nitrogen between them form phthalimido; or $R^1$ and $R^2$ together form a fused pyrazole of the formula

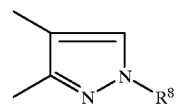

wherein $R^8$ is $C_{1-3}$-alkyl, or a fused thiadiazole of the formula

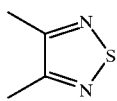

wherein $R^3$, $R^4$ and $R^5$ are as hereinbefore defined in this claim, or a pharmaceutically acceptable salt thereof.

2. The method for the treatment of urinary incontinence in accordance with claim 1, wherein, in the compound of the formulae Ib, $R^1$, $R^2$, $R^3$, $R^4$ and $R^5$ are each, independently of one another:

hydrogen, $C_{1-4}$-alkyl, cyclopropyl, $C_{1-4}$-alkoxy, halogen, —$CF_3$, —$OCF_3$, or —$NR^6R^7$, wherein;

$R^6$ is hydrogen, $C_{1-4}$-alkyl, $C_{3-6}$-cycloalkyl or acetyl;

$R^7$ is hydrogen, $C_{1-4}$-alkyl, cyclopropyl or acetyl; or, $R^6$ and $R^7$ together with the nitrogen between them form phthalimido; or $R^1$ and $R^2$ together form a fused pyrazole of the formula

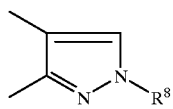

wherein $R^8$ is methyl, or a fused thiadiazole of the formula

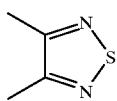

wherein $R^3$, $R^4$ and $R^5$ are as hereinbefore defined in this claim, or a pharmaceutically acceptable salt thereof.

3. The method for the treatment of urinary incontinence in accordance with claim 1, wherein, in the compound of the formulae Ib, $R^1$, $R^2$, $R^3$, $R^4$ and $R^5$ are each, independently of one another:

hydrogen, methyl, ethyl, cyclopropyl, fluorine, chlorine, bromine, —$CF_3$ or —$NR^6R^7$, wherein, $R^6$ is hydrogen, methyl or acetyl;

$R^7$ is hydrogen, methyl or acetyl; or, $R^6$ and $R^7$ together with the nitrogen between them form phthalimido; or $R^1$ and $R^2$ together form a fused pyrazole of the formula

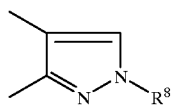

wherein $R^8$ is methyl, or a fused thiadiazole of the formula

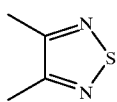

wherein $R^3$, $R^4$ and $R^5$ are as hereinbefore defined in this claim, or a pharmaceutically acceptable salt thereof.

4. The method for the treatment of urinary incontinence in accordance with claim 1, wherein, in the compound of the formulae Ib, $R^1$ is hydrogen, methyl, ethyl, fluorine, chlorine, bromine or —$CF_3$;

$R^2$ is methyl, fluorine, chlorine, bromine or —$NR^6R^7$, wherein;

$R^6$ is hydrogen, methyl or acetyl;

$R^7$ is hydrogen, methyl or acetyl; or, $R^6$ and $R^7$ together with the nitrogen between them form phthalimido;

$R^3$ is hydrogen, methyl, fluorine, chlorine, bromine, —$NH_2$ or cyclopropyl;

$R^4$ is hydrogen, methyl, fluorine, chlorine, bromine or $CF_3$;

$R^5$ is hydrogen, methyl, ethyl, fluorine, chlorine, bromine or $CF_3$; or, $R^1$ and $R^2$ together form a fused pyrazole of the formula

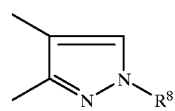

wherein $R^8$ is methyl, or a fused thiadiazole of the formula

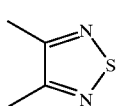

wherein $R^3$, $R^4$ and $R^5$ are as hereinbefore defined in this claim, or a pharmaceutically acceptable salt thereof.

5. The method for the treatment of urinary incontinence in accordance with claim 1, wherein, in the compound of the formulae lb, $R^1$ is hydrogen or methyl;

$R^2$ is methyl, chlorine, —$CF_3$, —$NH_2$ or —$N(CH_3)_2$;

$R^3$ is hydrogen, methyl, chlorine or bromine;

$R^4$ is hydrogen; and, $R^5$ is hydrogen, methyl, chlorine or bromine;

or a pharmaceutically acceptable salt thereof.

6. The method for the treatment of urinary incontinence in accordance with claim 1, wherein, the compound of the formulae lb is selected from the group consisting of:

2-(3-dimethylamino-2-methylphenylimino) imidazolidine;

2-(6-bromo-3-dimethylamino-2-methylphenylimino) imidazolidine;

2-(5-amino-2-chloro-4-dimethylamino-2-methylphenylimino)imidazolidine; and 2-(2-chloro-5-trifluoromethylphenylamino) imidazolidine, or is a pharmaceutically acceptable salt thereof.

7. A method for the treatment of urinary incontinence which comprises administering to a host in need of such treatment a therapeutically effective amount of an $\alpha_{1L}$-adrenoceptor agonist which is a compound of the formulae II

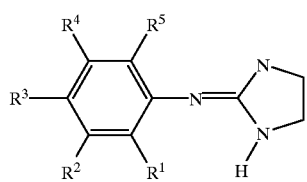

(II)

wherein
- $R^1$ is hydrogen, $C_{1-6}$-alkyl, $C_{3-6}$-cycloalkyl, $C_{1-6}$-alkoxy, halogen, —$CF_3$ or —$CF_3$;
- $R^2$ is —$NR^6R^7$, wherein,
- $R^6$ is hydrogen, $C_{1-6}$-alkyl, $C_{3-6}$-cycloalkyl or $C_{2-4}$-acyl;
- $R^7$ is hydrogen, $C_{1-6}$-alkyl, $C_{3-6}$-cycloalkyl or $C_{2-4}$-acyl; or,
- $R^6$ and $R^7$ together with the nitrogen between them form a 5- or 6-membered, saturated or unsaturated ring which may contain up to two additional heteroatoms selected from oxygen, sulfur and nitrogen, wherein each additional nitrogen atom is unsubstituted or substituted by $C_{1-4}$-alkyl, or $R^6$ and $R^7$ together with the nitrogen between them form phthalimido;
- $R^3$ is hydrogen, halogen, $C_{1-6}$alkyl, $C_{1-6}$-alkoxy, —$CF_3$ or —$OCF_3$;
- $R^4$ is hydrogen, halogen or $C_{1-6}$-alkyl; and,
- $R^5$ is hydrogen, $C_{1-6}$-alkyl, $C_{1-6}$-alkoxy, halogen, —$CF_3$ or $XCF_3$; or a pharmaceutically acceptable salt thereof.

8. The method for the treatment of urinary incontinence in accordance with claim 7, wherein, in the the compound of the formulae II,
- $R^1$ is hydrogen, $C_{1-4}$-alkyl, cyclopropyl, $C_{1-4}$-alkoxy, halogen, —$CF_3$ or —$OCF_3$;
- $R^2$ is —$NR^6R^7$, wherein,
- $R^6$ is hydrogen, $C_{1-4}$-alkyl, $C_{3-6}$-cycloalkyl or acetyl,
- $R^7$ is hydrogen, $C_{1-4}$-alkyl, $C_{3-6}$-cycloalkyl or acetyl, or,
- $R^6$ and $R^7$ together with the nitrogen between them form phthalimido;
- $R^3$ is hydrogen, halogen, $C_{1-4}$-alkyl, $C_{1-4}$-alkoxy, —$CF_3$ or $OCF_3$;
- $R^4$ is hydrogen, $C_{1-4}$-alkyl or halogen; and,
- $R^5$ is hydrogen, $C_{1-4}$-alkyl, $C_{1-4}$-alkoxy, halogen, —$CF_3$ or —$OCF_3$; or a pharmaceutically acceptable salt thereof.

9. The method for the treatment of urinary incontinence in accordance with claim 7, wherein, in the the compound of the formulae II,
- $R^1$ is hydrogen, $C_{1-3}$-alkyl, n-butyl, isobutyl, sec.-butyl, cyclopropyl, $C_{1-3}$-alkoxy, halogen or —$CF_3$;
- $R^2$ is —$NR^6R^7$, wherein,
- $R^6$ is hydrogen, $C_{1-4}$-alkyl or cyclopropyl,
- $R^7$ is hydrogen or $C_{1-4}$-alkyl, or,
- $R^6$ and $R^7$ together with the nitrogen between them form phthalimido;
- $R^3$ is hydrogen, $C_{1-3}$-alkyl, n-butyl, isobutyl, sec.-butyl, $C_{1-3}$-alkoxy, halogen or —$CF_3$;
- $R^4$ is hydrogen, $C_{1-3}$-alkyl, n-butyl, isobutyl, sec.-butyl, or halogen; and,
- $R^5$ is hydrogen, $C_{1-3}$-alkyl, n-butyl, isobutyl, sec.-butyl, $C_{1-3}$-alkoxy, halogen or —$CF_3$; or a pharmaceutically acceptable salt thereof.

10. A method for treating urinary incontinence which comprises administering to a host suffering from urinary incontinence a therapeutically effective amount of a compound selected from the group consisting of:
- 2-(3-dimethylamino-2-methylphenylimino) imidazolidine;
- 2-(6-bromo-3-dimethylamino-2-methylphenylimino) imidazolidine;
- 2-(5-amino-2-chloro-4-dimethylamino-2-methylphenylimino)imidazolidine; and
- 2-(3-amino-2-methylphenylimino)imidazolidine, or a pharmaceutically acceptable salt thereof.

11. A method for treating urinary incontinence which comprises administering to a host suffering from urinary incontinence a therapeutically effective amount of 2-(3-dimethylamino-2-methylphenylimino)imidazolidine, or a pharmaceutically acceptable salt thereof.

12. A method for treating urinary incontinence which comprises administering to a host suffering from urinary incontinence a therapeutically effective amount of 2-(6-bromo-3-dimethylamino-2-methylphenylimino) imidazolidine, or a pharmaceutically acceptable salt thereof.

13. A method for treating urinary incontinence which comprises administering to a host suffering from urinary incontinence a therapeutically effective amount of 2-(6-chloro-3-dimethylamino-2-methylphenylimino) imidazolidine, or a pharmaceutically acceptable salt thereof.

14. A method for the treatment of urinary incontinence which method comprises administering to a host suffering from urinary incontinence a therapeutically effective amount of tiamenidine.

* * * * *

UNITED STATES PATENT AND TRADEMARK OFFICE
CERTIFICATE OF CORRECTION

PATENT NO. : 6,268,389 B1
DATED : July 31, 2001
INVENTOR(S) : Franz Esser, Helmut Staehle, Sven Luettke, Ikunobu Muramatsu, Hisato Kitagawa and Shuji Uchida It is certified that error appears in the above-identified patent and that said Letters Patent is hereby corrected as shown below:

Column 1,
Line 26, "(XL" should read -- $\alpha_{IL}$ --.

Column 2,
Line 29, "$R^2_1$" should read -- $R^2$, --.
Line 34, "NR $R^7$" should read -- $NR^6R^7$ --.

Column 4,
Line 61, "R denotes" should read -- $R^2$ denotes --.

Column 5,
Line 6, delete the comma after "$R^6$"

Column 9,
Line 58, "dimetbylsulphate" should read -- dimethylsulphate --.

Column 11,
Line 42, "hydiodic" should read -- hydroiodic --.

Column 17,
Line 31, "$XCF_3$" should read -- $-OCF_3$ --.
Lines 33 and 51, "in the the compound" should read -- in the compound --.

Signed and Sealed this

Thirtieth Day of April, 2002

Attest:

Attesting Officer

JAMES E. ROGAN
Director of the United States Patent and Trademark Office